United States Patent
Juarez et al.

(10) Patent No.: US 10,488,369 B2
(45) Date of Patent: Nov. 26, 2019

(54) METHOD FOR CREATING A STRUCTURE FOR CALIBRATION OR VERIFICATION FOR NON-DESTRUCTIVE EVALUATION INSPECTION

(71) Applicant: U.S.A., as represented by the Administrator of the National Aeronautics and Space Administration, Washington, DC (US)

(72) Inventors: Peter D. Juarez, Hampton, VA (US); Cara A. C. Leckey, Poquoson, VA (US)

(73) Assignee: UNITED STATES OF AMERICA AS REPRESENTED BY THE ADMINISTRATOR OF NASA, Washington, DC (US)

( * ) Notice: Subject to any disclaimer, the term of this patent is extended or adjusted under 35 U.S.C. 154(b) by 216 days.

(21) Appl. No.: 15/480,977

(22) Filed: Apr. 6, 2017

(65) Prior Publication Data
US 2018/0292307 A1    Oct. 11, 2018

(51) Int. Cl.
*G01N 29/30* (2006.01)
*G01N 19/04* (2006.01)
(Continued)

(52) U.S. Cl.
CPC .......... *G01N 29/30* (2013.01); *G01N 15/088* (2013.01); *G01N 19/04* (2013.01); *G01N 19/08* (2013.01);
(Continued)

(58) Field of Classification Search
CPC ......... G01N 2001/2893; G01N 15/088; G01N 19/04; G01N 25/18; G01N 2021/8472;
(Continued)

(56) References Cited

U.S. PATENT DOCUMENTS 7,320,241 B2 *  1/2008  Kollgaard .............. G01N 29/30
                                                    73/1.86
8,287,681 B2 * 10/2012  Girshovich .......... G01N 29/043
                                                    156/252
(Continued)

FOREIGN PATENT DOCUMENTS

EP          2769834 A1 *  8/2014  ........... B29C 70/865

OTHER PUBLICATIONS

Waddell, M.C. "Comparison of Artificial Delamination Methods for us with Nondestructive Testing," Summary Report, 2013, University of New South Wales, Australia.
(Continued)

*Primary Examiner* — Nathaniel J Kolb
(74) *Attorney, Agent, or Firm* — Andrea Z. Warmbier; Robin W. Edwards; Helen M. Galus

(57) ABSTRACT

Various embodiment methods to reliably and repeatedly replicate delaminations/disbonds and/or porosity defects in specimens/structures may include constructing the specimens/structures such that aerogel sheets and/or aerogel powders are placed or deposited in selected delamination/disbonding and/or porosity locations in the specimen/structure before the specimen/structure is cured. In various embodiments, the specimens/structures may be composites and/or bonded structures and the structures may be flat or curved. The aerogel sheets and/or aerogel powders may mimic delamination/disbonding and/or porosity defects in the cured specimens/structures. The cured specimens/structures including the replicated aerogel sheets and/or aerogel powders may be used for nondestructive inspection or other measurements, such as POD studies.

18 Claims, 6 Drawing Sheets

(51) Int. Cl.
*G01N 15/08* (2006.01)
*G01N 19/08* (2006.01)
*B32B 7/12* (2006.01)
*G01N 1/28* (2006.01)

(52) U.S. Cl.
CPC ........ *B32B 7/12* (2013.01); *G01N 2001/2893* (2013.01); *G01N 2203/0298* (2013.01); *G01N 2291/0231* (2013.01); *G01N 2291/0289* (2013.01); *G01N 2291/2694* (2013.01)

(58) Field of Classification Search
CPC ............. G01N 2291/044; G01N 29/30; G01N 2203/0298; G01N 2291/0289; G01N 2291/0231; G01N 2291/2694
See application file for complete search history.

(56) References Cited

U.S. PATENT DOCUMENTS

| | | | | |
|---|---|---|---|---|
| 8,865,296 | B2* | 10/2014 | Chen | B32B 5/02 428/195.1 |
| 2007/0028661 | A1* | 2/2007 | Girshovich | G01N 29/043 73/1.01 |
| 2007/0101815 | A1* | 5/2007 | Kollgaard | G01N 29/30 73/618 |
| 2014/0272324 | A1* | 9/2014 | Chen | B32B 5/02 428/195.1 |

OTHER PUBLICATIONS

Castellini, P. et al., "Experimental Model of a Delamination within a Composite Panel: A Numerical Study," Marche Polytechnic University Department of Mechanics, 2005, Ancona, Italy.

Sundaravalli, S. et al., "Numerical Analysis of Defects in FML Using Through-Transmission Mode of Active Thermography," International Journal of Engineering Trends and Technology, 2012, p. 437-447, vol. 31(3).

Margetan, F.J. et al., Modeling the Effects of Beam Size and Flaw Morphology on Ultrasonic Pulse/Echo Sizing of Delaminations in Carbon Composites, 39th Annual Review of Progress in Quantitative Nondestructive Evaluation, AIP Conference Proceedings, Jan. 2013, pp. 955-962, vol. 1511, No. 1.

Birt, E.A. et al., A Review of NDE Methods for Porosity Measurement in Fibre-reinforced Polymer Composites, Insight-Non-Destructive Testing and Condition Monitoring, 2004, pp. 681-686, vol. 46(11).

\* cited by examiner

METHOD FOR CREATING A STRUCTURE FOR CALIBRATION OR VERIFICATION FOR NON-DESTRUCTIVE EVALUATION INSPECTION

STATEMENT REGARDING FEDERALLY SPONSORED RESEARCH OR DEVELOPMENT

The invention described herein was made by employees of the United States Government and may be manufactured and used by or for the Government of the United States of America for governmental purposes without the payment of any royalties thereon or therefore.

BACKGROUND OF THE INVENTION

Defect standards are essential to validate and calibrate new and traditional inspection techniques. Inspection techniques require nondestructive evaluation (NDE) standards with known and well-characterized defects to be used in testing that establishes confidence that the particular defect can be detected in a real world setting. Probability of detection (POD) studies also require accurate representations of defects in test specimen (i.e., test standards) in order to represent the physics of inspection energy interaction with the defect. Current defect standards do not effectively represent porosity and delaminations/disbonds. Porosity and delamination/disbond in composites are difficult to represent in standards at this time and there is currently no established adequate method that is well controlled, representative of delamination/porosity defects, and is transferable across the most common NDE inspection techniques.

BRIEF SUMMARY OF THE INVENTION

The various embodiments address an urgent need for more accurate, reliable, and well controlled methods to represent porosity and/or delamination defects in composites and adhesives. In various embodiments, solids and/or particulates may be introduced into composites and/or adhesives while the composites and/or adhesives are being constructed and the solids and/or particulates survive as the structure/specimen is cured. Once cured, the solid and/or particulate additive may behave as a delamination and/or porosity defect, and may be indistinguishable from real delamination and/or porosity defects when inspected with popular nondestructive evaluation techniques, such as ultrasound, thermography, etc. In this manner, the solid and/or particulate additive may be a representative defect. The various embodiments may provide predictable and repeatable methods to replicate difficult defects in composites and bonded structures, such as porosity and/or delamination. Not only can the attributes of these difficult defects, such as porosity and/or delamination, be well controlled in the various embodiments, but the embodiment simulated (or representative) defects may also behave as real-world defects when inspected by multiple types of nondestructive evaluation techniques.

Various embodiments may provide methods for creating a representative defect in a structure/specimen, including selecting one or more defect locations in the structure/specimen, constructing the structure/specimen including placing aerogel at the selected defect locations, and curing the structure/specimen. The various embodiments may provide structures/specimens that may be composite and/or adhesive structures with aerogel sheets and/or aerogel powders at selected delamination and/or porosity locations.

Various embodiment methods to reliably and repeatedly replicate delaminations/disbonding and/or porosity defects in specimens/structures may include constructing the specimens/structures such that aerogel sheets and/or aerogel powders are placed or deposited in selected delamination/disbonding and/or porosity locations in the specimen/structure before the specimen/structure is cured. In various embodiments, the specimens/structures may be composites and/or bonded structures and the structures may be flat or curved. The aerogel sheets and/or aerogel powders may mimic delamination/disbonding and/or porosity defects in the cured structures/specimens, thereby operating as representative defects. The cured specimens/structures including the replicated aerogel sheets and/or aerogel powders may be used for measurements, such as POD studies. Measurements of the cured specimens/structures including the replicated aerogel sheets and/or aerogel powders may include applying one or more non-destructive evaluation techniques, such as ultrasound, thermography, etc., to the specimens/structures to measure how the mimicked delamination/disbonding and/or porosity defects behave during non-destructive evaluation, as well as the capability of the non-destructive evaluation techniques to detect the representative delamination/disbonding and/or porosity defects. The measurements may enable porosity and delamination/disbonding defects to be represented in standards. The ability to reliably and repeatedly replicate delaminations/disbonding and/or porosity defects in specimens/structures may enable validation and/or calibration of non-destructive inspection techniques.

These and other features, advantages, and objects of the present invention will be further understood and appreciated by those skilled in the art by reference to the following specification, claims, and appended drawings.

BRIEF DESCRIPTION OF THE SEVERAL VIEWS OF THE DRAWINGS

The accompanying drawings, which are incorporated herein and constitute part of this specification, illustrate exemplary embodiments of the invention, and together with the general description given above and the detailed description given below, serve to explain the features of the invention.

DETAILED DESCRIPTION OF THE INVENTION

Figure 1:
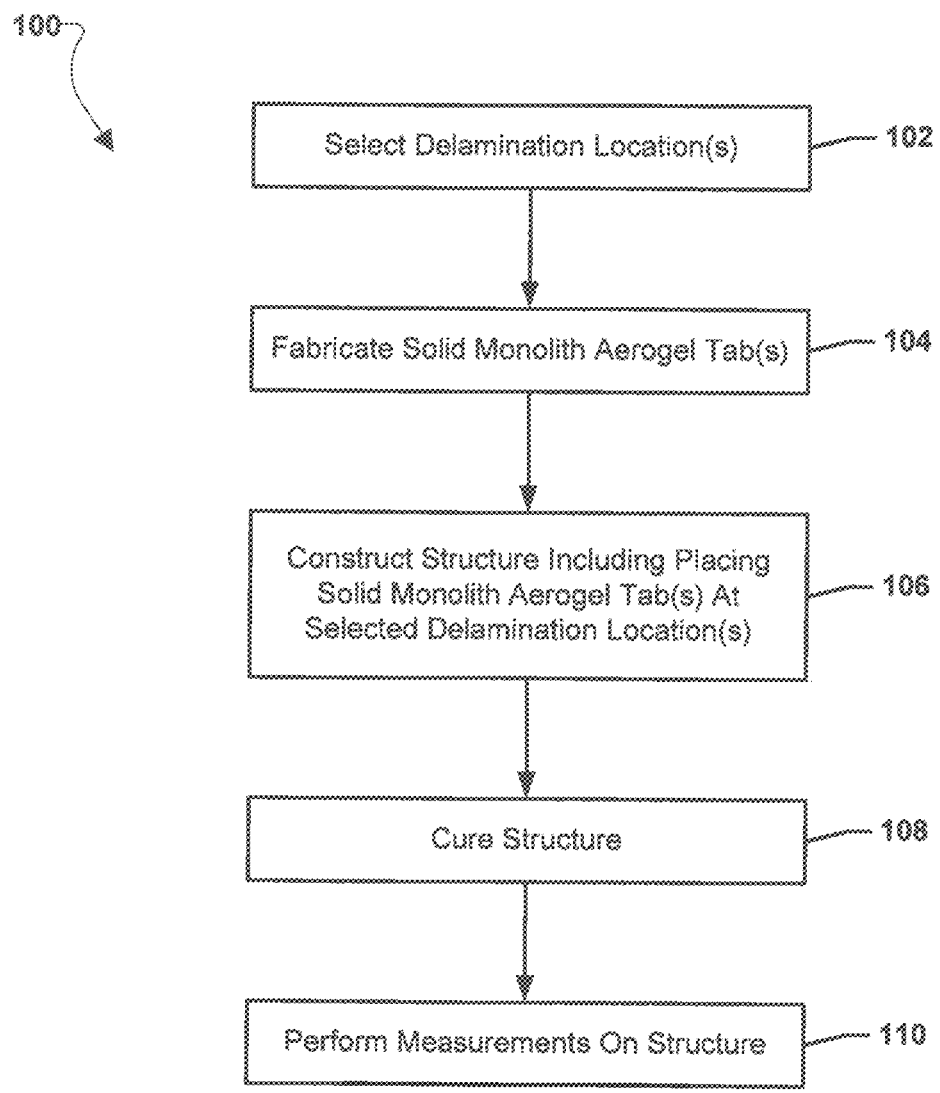
FIG. 1 is a process flow diagram illustrating an embodiment method for creating delamination defects in structures.

It is to be understood that the invention may assume various alternative orientations and step sequences, except where expressly specified to the contrary. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Porosity occurs in composites during the curing process when small gas (e.g., air, etc.) bubbles occur in the fiber-resin mixture. Porosity can severely reduce structural integrity. These same porosity effects can also apply to adhesive layers in bonded structures, where small gas (e.g., air, etc.) bubbles are created during the bonding process.

Delaminations (also referred to as disbonds) in composites may occur during curing or after curing due to impact or high load events and develop as thin layers of debond between different ply layers. Delamination/disbonds also decreases structural integrity.

Currently, there is no standard methodology to accurately and repeatedly create porosity in composites or bonded structures. Currently, one way to attempt to recreate porosity is to adjust curing parameters (such as temperature and pressure) with the intent to create porosity effects. The issue with adjusting the cure cycle to create porosity may be that there is a large variability in the curing parameters. As a result adjusting the curing parameters does not always create porosity, and when adjusting the curing parameters does create porosity, the porosity is not created in a known, controlled, or repeatable quantity (i.e., percent porosity). Small gas-filled glass beads (e.g., air-filled glass beads) have also been experimented with to recreate porosity. Though glass beads have been experimented with, the glass beads have a tendency to melt and pool together and increase volume of the composite locally causing unwanted surface deformations.

There exist methods to recreate delaminations/disbonds, but the methods are sometimes specific to certain inspection methods and suffer from poor repeatability and/or have poor control of defect characteristics. Methods to create delamination/disbond simulants in composites prior to curing include the use of Polytetrafluoroethylene (PTFE) inserts, PTFE gas (e.g., air) pillows, pull-out tabs, and indentation. For cured composites impact based methods are used to create delamination defects. The impact based methods do not allow for control of defect size and/or may create defect of unknown characteristics. PTFE inserts work well for pulse-echo ultrasound, but do not work as well for thermography. Teflon® inserts and gas (e.g., air) pillows also have a tendency to melt and pool in certain areas during the curing process, which makes ensuring the intended shape and behavior of the defect difficult to achieve with Teflon® inserts or Teflon® gas pillows. As another example, indentations often close up during the curing process. As a further example, pull-out tabs sometimes damage the material when the pull-out tabs are being removed, and can also only be used at the edge of NDE standards (i.e., edges of the test article).

Various embodiments use the unique properties of aerogel to reliably and repeatedly replicate defects, such as porosity and/or delamination, for testing of specimens/structures formed from composites and/or adhesives according to defects standards.

Aerogel is a silica material that has one of the lowest densities of any solid ever made. For example, a solid monolith of aerogel may be 98.2% gas (e.g., air, etc.) by volume, has a density of 2.2 Kg/m$^3$ and a thermal effusivity equivalent to air. Since porosity and delaminations are similar to small gas (e.g., air, etc.) gaps or gas (e.g., air, etc.) bubbles, aerogel enables the insertion of solid gas (e.g., air, etc.) into a composite and/or adhesive to replicate the gas (e.g., air, etc.) effects. Aerogel also has the ability to withstand the high temperatures used in most composite cure cycles, such as temperatures greater than 300° C. Since the effectiveness of aerogel as the defect simulant is related to the density and porous nature of the aerogel, other types of aerogel materials may be used (such as carbon aerogel), provided the density and porous nature is similar to that of silica-based aerogel.

Various embodiments may provide methods for creating a representative (or simulated) defect in a specimen/structure, including selecting one or more defect locations in the specimen/structure, constructing the specimen/structure including placing aerogel at the selected defect locations, and curing the specimen/structure.

Various methods to reliably and repeatedly replicate defects, such as delaminations/disbonds and/or porosity defects, in specimens/structures may include constructing the specimens/structures such that aerogel sheets and/or aerogel powders are placed or deposited in selected defect locations, such as delamination/disbonding and/or porosity locations, in the specimen/structure before the specimen/structure is cured. In various embodiments, the specimens/structures may be composites and/or bonded structures and the structures may be flat or curved. The aerogel sheets and/or aerogel powders may mimic delamination/disbonding and/or porosity defects in the cured specimens/structures. In this manner, the aerogel sheets and/or aerogel powders may be representative (or simulated) delamination/disbonding and/or porosity defects. The cured specimens/structures including the replicated aerogel sheets and/or aerogel powders may be used for measurements, such as POD studies. Measurements of the cured specimens/structures including the replicated aerogel sheets and/or aerogel powders may include applying one or more non-destructive evaluation techniques, such as ultrasound, thermography, etc., to the specimens/structures to measure how the mimicked delamination/disbonding and/or porosity defects behave during non-destructive evaluation, as well as the capability of the non-destructive evaluation techniques to detect the mimicked delamination/disbonding and/or porosity defects. The measurements may enable porosity and delamination/disbonding defects to be represented in standards. The ability to reliably and repeatedly replicate delaminations/disbonds and/or porosity defects in specimens/structures may enable validation and/or calibration of non-destructive inspection techniques Various examples of different gases are discussed herein, such as air. The discussions of air and other gases are provided merely as examples to better illustrate the aspects of the various embodiments, and are not intended to limit the scope of the disclosure or the claims in any way. Other gases, such as nitrogen, argon, gas mixes, etc., may be used with the various embodiments, and the other gases may be substituted in the various examples without departing from the spirit or scope of the invention.

FIG. 1 illustrates an embodiment method 100 for creating delamination defects in specimens/structures, such as composite structures and/or bonded structures. The method 100 may include selecting one or more delamination/disbonding locations in step 102. As examples, the delamination/disbonding locations may be above or below selected ply layers, above or below selected adhesive layers, selected ply layers themselves, selected adhesive layers themselves, at selected depths within ply and/or adhesive layers, and/or at selected spatial areas on or within ply and/or adhesive layers in a composite and/or bonded structure. The delamination/disbonding locations may be selected to create standard defects for validating and calibrating inspection techniques. The delamination/disbonding locations may provide well characterized defects to test against to certify that the selected particular defect can be detected and to assist in POD studies by accurately reproducing defects of interest in the specimen/structure such that the specimen/structure acts as a test article.

In step 104 one or more solid monolith aerogel sheets may be fabricated. Solid monoliths of aerogel may be fabricated to very thin sheets, such as sheets less than 1 millimeter (mm) thick. In some embodiments, the thickness of the aerogel sheet may be selected such that the thickness of the aerogel sheet is less than a ply thickness of the specimen/structure itself. For example, in the case of creating delamination type defect in a composite laminate with ply thicknesses around 125 microns, it may be appropriate to use thin aerogel sheets less than the ply thickness, such as thin aerogel sheets with a thickness less than 125 microns. The appropriate thickness of aerogel sheet may be application dependent. The fabrication of the aerogel sheets may be done either during the formation of the aerogel or in machining of a larger aerogel monolith. To prevent resin from infusing into the sheets of the aerogel and displacing the gas (e.g., air, etc.), methods known in the aerogel industry may be utilized to give the precipitated aerogel powder a hydrophobic surface.

In step 106 the structure/specimen may be constructed including placing the solid monolith aerogel sheets at the selected delamination locations. For example, the aerogel sheets may be laid on a ply layer during layup of the composite at a selected ply depth and spatial location. The rest of the structure/specimen may be constructed and then cured, for example in an autoclave, in step 108. After curing the aerogel sheer inserted in the structure/specimen may completely mimic a thin gas gap (e.g., air gap, etc.), such as less than 1 mm, thick between the ply layer only at the region the aerogel sheet was located. The resulting specimen/structure may be a composite and/or adhesive structure with aerogel sheets at selected delamination locations.

In step 110 measurements may be performed on the specimen/structure including the aerogel sheet. The aerogel sheet may be a large acoustic impedance mismatch in the composites, meaning the aerogel sheet may respond like a delamination/disbonding defect in all acoustic-based measurements. Additionally, because the aerogel sheets has a thermal effusivity similar to that of air, the aerogel sheets may also respond like a delamination/disbonding defect in thermal-based inspections. In this manner, the aerogel sheets at the selected delamination/disbonding locations may create standard defects for validating and calibrating inspection techniques. The specimen/structure including the aerogel sheets at the selected delamination/disbonding locations may provide well characterized defects to test against to certify that the selected particular defect can be detected and to assist in POD studies by accurately reproducing defects of interest in the structure such that the specimen/structure acts as a test article.

Figure 2:
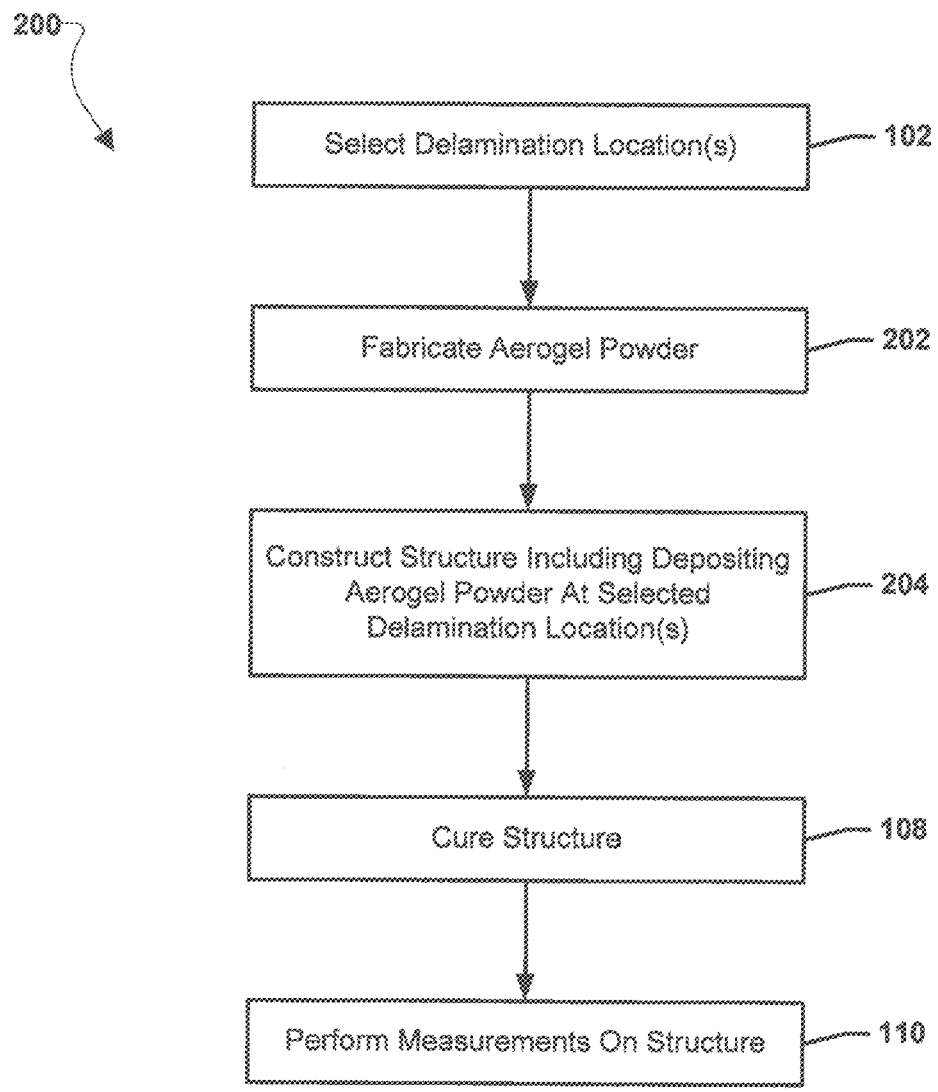
FIG. 2 is a process flow diagram illustrating an embodiment method for creating delamination defects in structures.

FIG. 2 is illustrates an embodiment method 200 for creating delamination defects in specimens/structures. The method 200 is similar to method 100 described above, except aerogel powder may be used to create delamination defects. In various embodiments, the operations of method 200 may be performed in conjunction with the operations of method 100 described above. Method 200 may be suitable for creating delaminations/disbonds in composite and/or bonded structures that may be flat and/or curved. The method 200 may include selecting one or more delamination/disbonding locations in step 102, as described above with reference to method 100.

In step 202, aerogel powder may be fabricated. For example, known aerogel manufacturing techniques may be utilized to yield very fine particulate powder of precipitated aerogel. To prevent resin from infusing into the pores of the aerogel and displacing the gas (e.g., air, etc.), methods known in the aerogel industry may be utilized to give the precipitated aerogel powder a hydrophobic surface. In step 204, the specimen/structure may be constructed including depositing the aerogel powder at the selected delamination/disbonding locations. For example, the aerogel powder may be deposited on the part during fabrication, either during the ply layup process or during specimen/structure bonding. The thin layer of powder, which for example in composite specimens/structures may be less than the ply thickness (e.g., less than approximately 125 microns), may be held together by the resin or the adhesive and the fabrication may continue as normal once the aerogel powder is deposited. The resulting specimen/structure may be a composite and/or adhesive structure with aerogel powder at selected delamination/disbonding locations. In steps 108 and 110, the specimen/structure is cured and measurements are performed in a similar manner as discussed above with reference to method 100. For example, the aerogel powder may be a large acoustic impedance mismatch in the composites, meaning the aerogel powder may respond like a delamination/disbonding defect in all acoustic-based measurements. Additionally, because the aerogel powder has a thermal effusivity similar to that of air, the aerogel powder may also respond like a delamination/disbonding defect in thermal-based inspections. In this manner, the aerogel powder at the selected delamination/disbonding locations may create standard defects for validating and calibrating inspection techniques. The specimen/structure including the aerogel powder at the selected delamination/disbonding locations may provide well characterized defects to test against to certify that the selected particular defect can be detected and to assist in POD studies by accurately reproducing defects of interest in the specimen/structure such that the structure acts as a test article.

Figure 3:
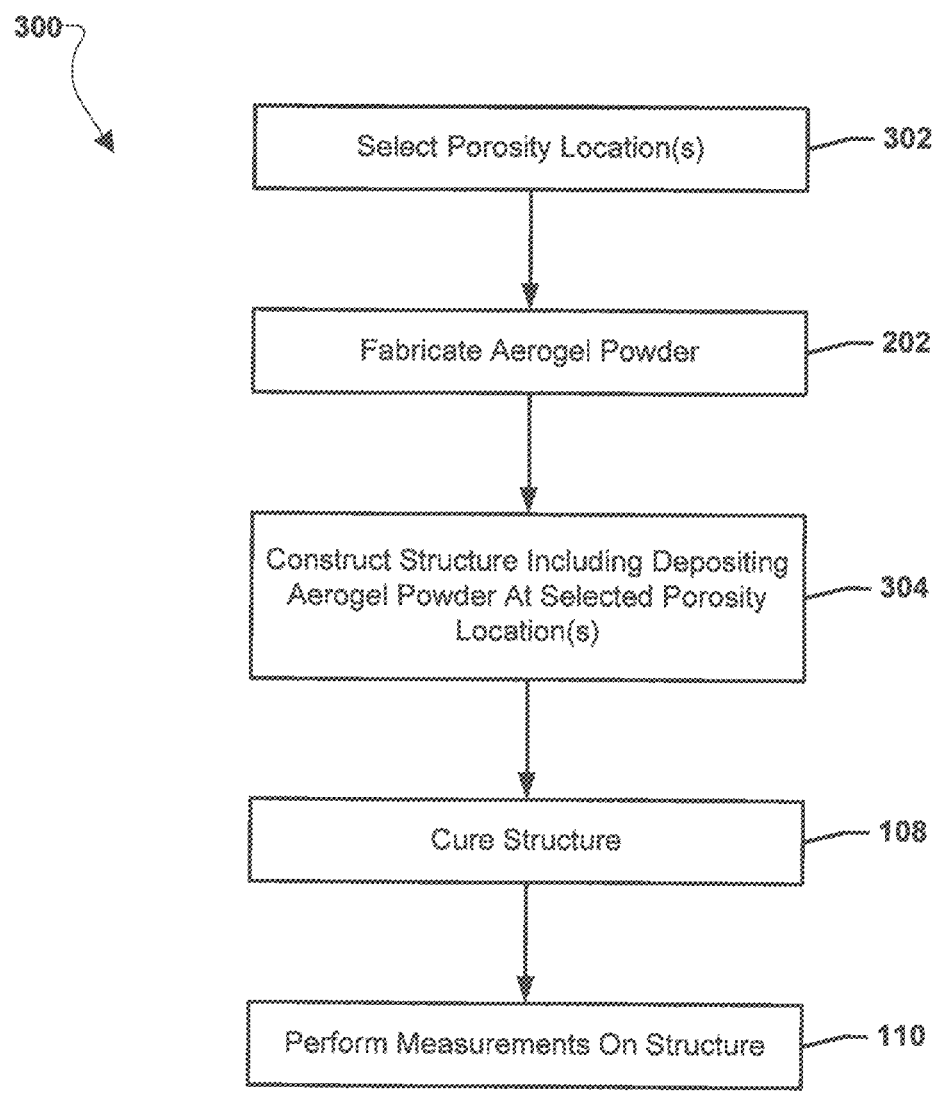
FIG. 3 is a process flow diagram illustrating an embodiment method for creating porosity defects in structures.

FIG. 3 illustrates an embodiment method 300 for creating porosity defects in specimens/structures. The method 300 is similar to methods 100 and 200 described above, except aerogel powder may be used to create porosity defects. In various embodiments, the operations of method 300 may be performed in conjunction with the operations of methods 100 and/or 200 described above. Method 300 may be suitable for creating porosity defects in composite and/or bonded structures. For example, porosity defects may be created by powder particles of sixes 10 to 50 microns. Larger particle sizes may also be used to simulate larger pores.

The method 300 may include selecting one or more porosity locations in step 302. As examples, the porosity locations may be above or below selected ply layers, above or below selected adhesive layers, selected ply layers themselves, selected adhesive layers themselves, at selected depths within ply and/or adhesive layers, and/or at selected spatial areas on or within ply and/or adhesive layers in a composite and/or bonded structure. The porosity locations may be selected to create standard defects for validating and calibrating inspection techniques. The porosity locations may provide well characterized defects to test against to certify that the selected particular defect can be detected and to assist in POD studies by accurately reproducing defects of interest in the specimen/structure such that the specimen/structure acts as a test article. The method 300 may include fabricating powdered aerogel in step 202, as described above with reference to method 200.

In step 304, the specimen/structure may be constructed including depositing the aerogel powder at the selected porosity locations. For example, to replicate porosity the powder may be deposited into a composite in a small designated area on a ply-by-ply basis during layup. The selected distribution of the aerogel powder may be achieved using a sift device, or other device capable of applying a controlled amount of aerogel powder evenly and within the desired simulated defect region. As another example, for adhesives, the aerogel powder may be mixed with the desired volume of adhesive prior to application and bonding. In various embodiments, for ply layers and/or adhesive layers, a calculation may be made to determine how much aerogel powder may be needed to attain a desired percent porosity. For bonded structures this calculation may be as:

$$Va = Vi\, X/(100-X)$$

where, Va=Volume of aerogel needed, Vi=initial volume of adhesive that will have porosity, and X is the percent porosity desired. For porosity in composites or layered specimen/structures (such as adhesively bonded layered specimen), if it is desired to create representative porosity at multiple plies/layers through the specimen/structure thickness, the volume of aerogel needed per ply/layer may be calculated as:

$$Va(Vi(X/(100-X))/(n-1)$$

where, Va=Volume of aerogel needed per ply, Vi=initial volume of the composite to contain porosity or volume of adhesive that will have porosity, X is the percent porosity desired and n is the number of plies/layers desired, for containing porosity. The resulting specimen/structure may be a composite and/or adhesive structure with aerogel powder at selected porosity locations.

In steps 108 and 110, the specimen/structure is cured and measurements are performed in a similar manner as discussed above with reference to methods 100 and 200. For example, the aerogel powder may be a large acoustic impedance mismatch in the composites, meaning the aerogel powder may respond like a porosity defect in all acoustic-based measurements. Additionally, because the aerogel powder may be very good insulators, the aerogel powder may also respond like a porosity defect in thermal-based inspections. In this manner, the aerogel powder at the selected porosity locations may create standard defects for validating and calibrating inspection techniques. The specimen/structure including the aerogel powder at the selected porosity locations may provide well characterized defects to test against to certify that the selected particular defect can be detected and to assist in POD studies by accurately reproducing defects of interest in the specimen/structure such that the specimen/structure acts as a test article.

Figure 4:
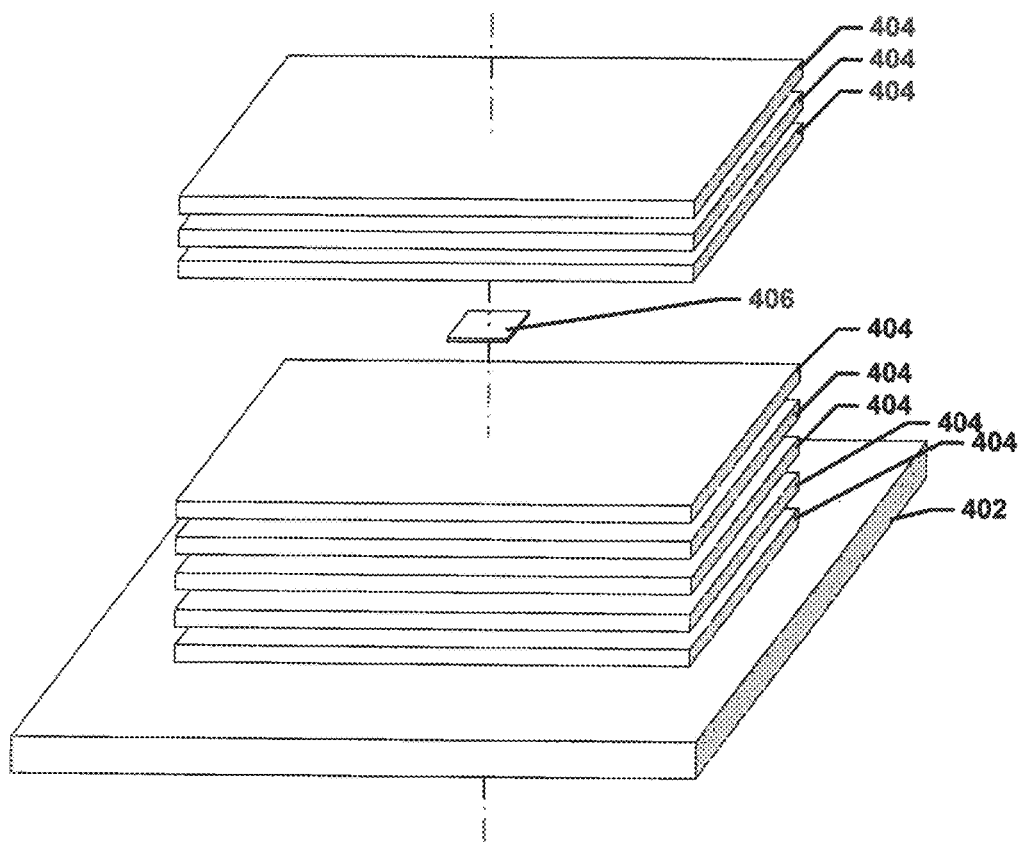
FIG. 4 is an exploded view block diagram illustrating an example of aerogel sheet insertion between plies during layup according to an embodiment.

FIG. 4 illustrates an aerogel sheet 406 inserted between plies 404 of a specimen/structure during layup according to an embodiment. As the composite layers 404 are laid down on the tooling surface 402, the aerogel sheet 406 may be placed at the selected delamination/disbonding location and additional composite layers 404 may be added to the specimen/structure. The structure/specimen may then be cured and the aerogel sheet 406 may act as a representative defect, such as a delamination/disbanding defect, in the structure/specimen.

Figure 5:
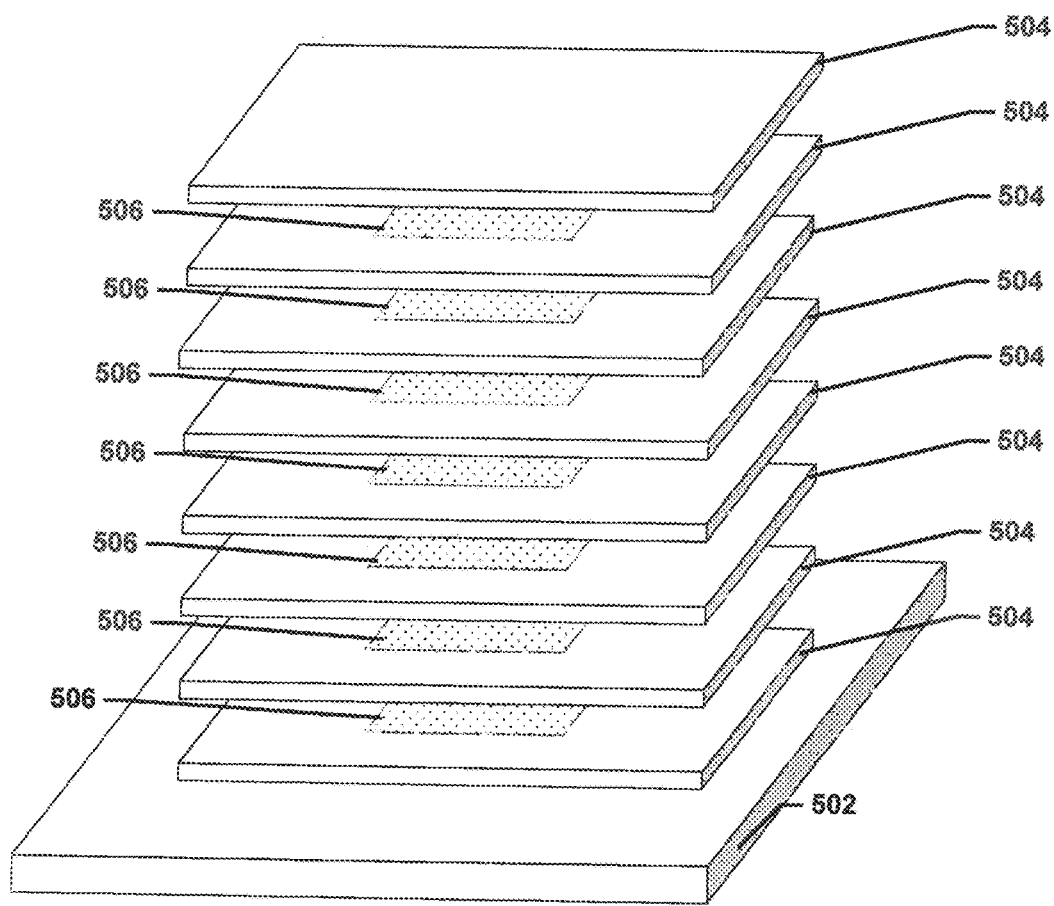
FIG. 5 is an exploded view block diagram illustrating an example of aerogel powder insertion between plies during layup according to an embodiment.

FIG. 5 illustrates aerogel powder 506 insertion between plies 504 of a specimen/structure during layup according to an embodiment. As the composite layers 504 are laid down on the tooling surface 502, aerogel powder 506 may be placed at selected porosity locations and additional composite layers 504 may be added to the structure/specimen. For example, aerogel powder 506 may be added between each composite layer 504 to simulate through-thickness porosity in the structure/specimen. The structure/specimen may then be cured and the aerogel powder 506 may act as a representative defect, such as a porosity defect, in the structure/specimen.

Figure 6:
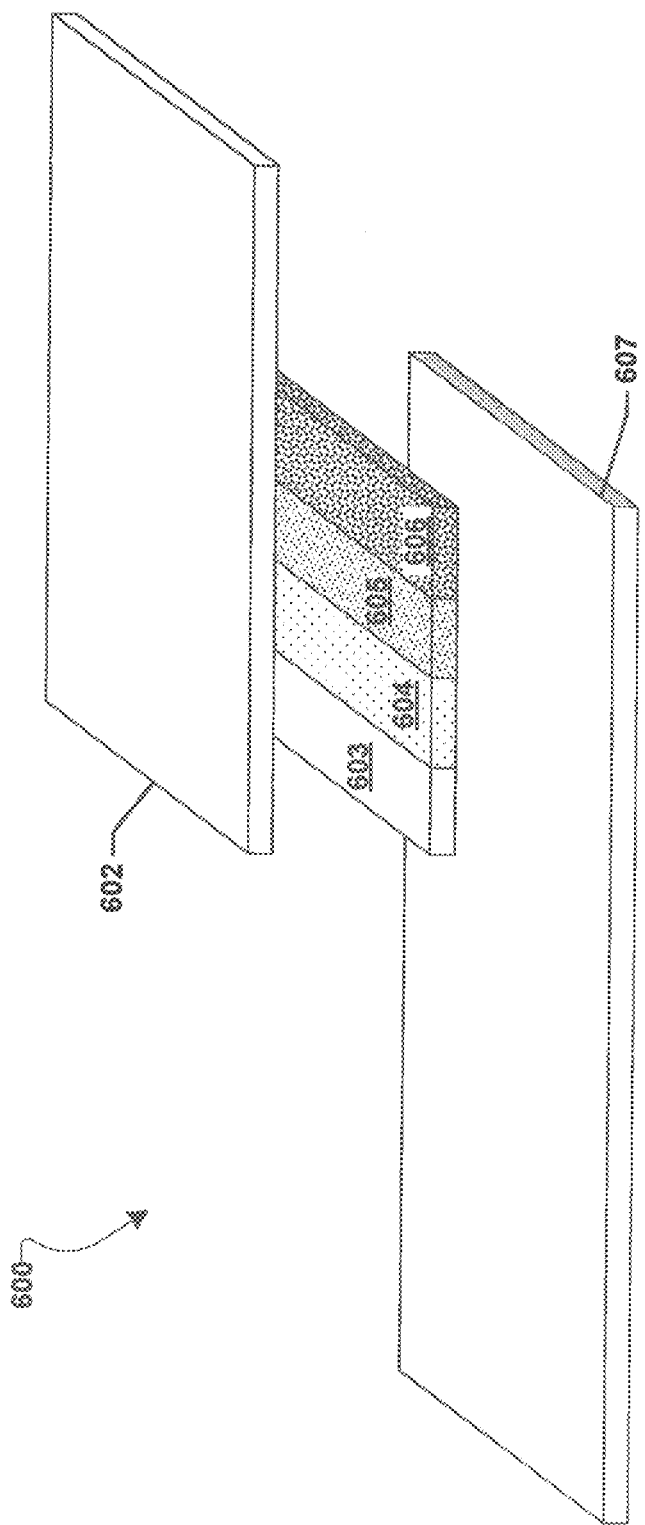
FIG. 6 is an exploded view block diagram illustrating an example of using aerogel powder according to an embodiment.

FIG. 6 illustrates a lap joint 600 constructed according to an embodiment. The lap joint 600 may include a first layer 602 joined to a second layer 607 by adhesive mixtures 603, 604, 605, and 606. The adhesive mixtures 603, 604, 605, and 606 may be different compositions of adhesive and adhesive pre-mixed with aerogel powder. For example, adhesive mixture 603 may be adhesive with no aerogel powder and adhesive mixtures 604, 605, and 606 may be pre-prepared mixtures of adhesive with different relative amounts of aerogel powder to simulate varying degrees of porosity across the different adhesive mixtures 603, 604, 605, and 606 (e.g., 603 may simulate no porosity, 604 may simulate some porosity, 605 may simulate greater porosity than 604, and 606 may simulate greater porosity than 604 and/or 605). The location of the adhesive mixtures 604, 605, and 606 may be at selected porosity locations in the lap joint 600. In the example discussed above, the lap joint 600 may then be cured and the adhesive mixtures 604, 605, and 606 may act as representative defects at their respective locations, such as different porosity defects in the lap joint 600, while the adhesive mixture 603 may act as a control with no simulated porosity defects present at its location in the lap joint 600.

The various embodiments may enable delamination/disbonds and/or porosity defects to be simulated and measured in various structures, such as aerospace structures (e.g., aircraft joints and skins, spacecraft joints, skins, heat shields, etc.), oil and gas structures, automotive structures, etc. The various embodiments may enable composite and bonded parts to undergo certification and calibration measurements as part of Probability of Detection (POD) studies. The various embodiments may enable better characterized defect standards such that the abilities and limitations of inspection techniques may be known to a much higher degree of accuracy than currently possible.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein bin is to be accorded the widest scope consistent with the following claims and the principles and novel features disclosed herein.

What is claimed is:

1. A method of fabricating a composite or bonded structure having at least one representative defect, comprising:
   selecting one or more defect locations in a structure to be fabricated, wherein the defect locations are selected prior to completing fabrication of the structure;
   fabricating the structure from one or more materials including at least one curable material, wherein fabricating the structure includes placing aerogel at one or more of the selected defect locations followed by curing the curable material of the structure whereby the aerogel forms a representative defect in the structure.

2. The method of claim 1, wherein fabricating the structure includes laying up a plurality of ply layers to form a composite structure, and wherein the aerogel is configured to replicate a delamination defect in the composite structure.

3. The method of claim 2, wherein fabricating the composite structure includes placing at least one aerogel sheet between at least two ply layers.

4. The method of claim 3, wherein the at least one aerogel sheet includes a hydrophobic coating.

5. The method of claim 3, wherein at least one of the ply layers has a ply thickness, and wherein a thickness of the least one aerogel sheet is less than the ply thickness.

6. The method of claim 2, wherein fabricating the composite structure includes depositing aerogel powder to replicate a delamination defect in the composite structure.

7. The method of claim 1, wherein the structure is a bonded structure that is fabricated by adhesively bonding a first member to a second member with curable adhesive material.

8. The method of claim 1, wherein the aerogel is configured to replicate porosity defect.

9. The method of claim 8, including depositing aerogel powder to replicate a porosity defect.

10. The method of claim 9, wherein the structure is fabricate from a plurality of ply layers, and wherein aerogel powder is deposited on one or more ply layers during layup of the structure.

11. The method of claim 7, wherein the aerogel powder is mixed with the curable adhesive prior to curing the adhesive material.

12. The method of claim 8, wherein the structure is a bonded structure that is fabricated by adhesively bonding a first member to a second member with curable adhesive material.

13. The method of claim 1, further comprising performing a non-destructive measurement on the structure after the curable material is cured to detect the representative defect formed by the aerogel.

14. A method of fabricating a measurement structure, comprising:
    fabricating the measurement structure from one or more layers and a curable material;
    wherein fabricating the measurements structure includes disposing aerogel in the measurement structure at a selected location relative to the one or more layers prior to curing the curable material followed by curing the curable material such that the aerogel replicates a defect in the measurement structure.

15. The method of claim 14, wherein the aerogel is configured to replicate at least one of a porosity defect and a delamination defect.

16. The method of claim 15, wherein the aerogel comprises one or more aerogel sheets or aerogel powder.

17. The method of claim 15, wherein fabricating the measurements structure comprises at least one of a) laying up a plurality of ply layers to form a composite measurement structure, or b) adhesively bonding first and second layers together using a curable adhesive to form a bonded measurement structure.

18. The method of claim 14, including adhering the one or more layers together with an adhesive layer.

* * * * *